(12) United States Patent
Millard

(10) Patent No.: US 8,921,601 B2
(45) Date of Patent: Dec. 30, 2014

(54) PROCESS FOR RECOVERY OF ALKANOLAMINES USED IN AMINE SWEETENING PROCESSES

(71) Applicant: Michael G. Millard, Evansville, IN (US)

(72) Inventor: Michael G. Millard, Evansville, IN (US)

(73) Assignee: Chem Group, Inc., Evansville, IN (US)

( * ) Notice: Subject to any disclaimer, the term of this patent is extended or adjusted under 35 U.S.C. 154(b) by 0 days.

(21) Appl. No.: 13/737,435

(22) Filed: Jan. 9, 2013

(65) Prior Publication Data

US 2014/0194652 A1    Jul. 10, 2014

(51) Int. Cl.
*C07C 213/02* (2006.01)
*C07C 213/00* (2006.01)

(52) U.S. Cl.
CPC .................................. *C07C 213/02* (2013.01)
USPC ........................................ 564/497; 564/498

(58) Field of Classification Search
CPC ................................................. C07C 213/10
USPC ................................................... 564/497, 498
See application file for complete search history.

(56) References Cited

U.S. PATENT DOCUMENTS

| | | | | |
|---|---|---|---|---|
| 2,797,188 A | * | 6/1957 | Taylor, Jr et al. | 208/236 |
| 4,650,906 A | * | 3/1987 | Murakami et al. | 564/498 |
| 4,683,337 A | * | 7/1987 | Budde | 564/498 |
| 4,798,910 A | * | 1/1989 | Herrin | 564/497 |
| 5,108,551 A | * | 4/1992 | Yan | 203/6 |
| 5,137,702 A | * | 8/1992 | Yan | 423/229 |
| 5,389,208 A | * | 2/1995 | Beasley et al. | 203/11 |

* cited by examiner

*Primary Examiner* — Brian J Davis
(74) *Attorney, Agent, or Firm* — Bushman Werner, P.C.

(57) ABSTRACT

A process for recovering an alkanolamine from a used gas scrubbing stream wherein a dynamic reaction system is employed to maximize conversion of bis-urea compounds typically formed in the gas scrubbing operation into the alkanolamine and minimize the formation of amino ethers which irreversibly convert the alkanolamine. A method of removing waste products from the system by the use of a wiped film evaporator.

18 Claims, 3 Drawing Sheets

PROCESS FOR RECOVERY OF ALKANOLAMINES USED IN AMINE SWEETENING PROCESSES

FIELD OF THE INVENTION

The present invention relates to the recovery of alkanolamines from wash or scrubbing streams used to remove acid gasses from gas streams. More particularly, the present invention relates to such a process in which carbamates formed during the gas scrubbing operation are converted back to the alkanolamine.

BACKGROUND OF THE INVENTION

The removal of acid gases, e.g. hydrogen sulfide, carbonyl sulfide, and carbon dioxide, from industrial and natural gas streams is an important and frequently encountered operation in the process industry. It is known that in these processes, certain of the alkanol amines used react with carbon dioxide to form carbamate precursors. The formation of the carbamate precursors is detrimental to the scrubbing process since they can cause corrosion, have no acid gas removal properties and reduce solution capacity.

Historically, thermal reclaimers have been used to remove nonvolatile contaminants from the used scrubbing or wash solution. However, these thermal reclaimers pose difficulties in that high temperatures, long residence time, and dehydrating environment are typically encountered in such reclaimers. Moreover, there are many problems with conventional reclaimer designs and operations. In particular, in the high temperature dehydrating environment encountered in conventional thermal reclaimers, the carbamate precursors can be converted into amino ethers with permanent, concomitant loss of the alkanolamine. This presents a large problem since major loss of the alkanolamine translates into significant chemical replacement costs in the overall gas scrubbing operation. It is known that the production of these amine ethers in conventional recovery processes is accelerated by increased temperature and exposed residence times in the reclaimer.

Using diglycolamine (DGA) as an example, in the scrubbing operation, the DGA reacts with $CO_2$ to form a carbamate precursor. The carbamate precursor can react with DGA to form N,N,bis(hydroxyethoxyethyl)urea (BHEEU). The BHEEU, at the high temperatures in a typical thermal reclaimer, can irreversibly degrade to morpholine, an amino ether, and DGA. Accordingly, there is a net loss of DGA from the system.

The equations below show the reaction sequence:

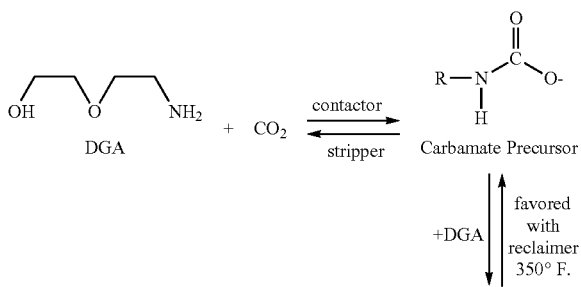

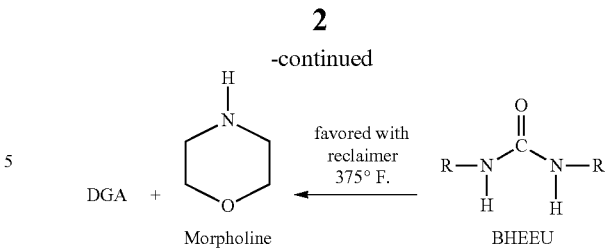

FIG. 3 is a graph taken from a paper entitled Saudi Arabian Experience with DGA Units and Related Sulfur Plants, by Lewis G. Harruff, Saudi Arabian Oil Co. It shows the relationship between morpholine make, temperature and residence time.

SUMMARY OF THE INVENTION

In one aspect, the present invention provides a continuous process for recovering an alkanolamine from a wash or scrubbing stream used to remove acid gases from gas streams.

In another aspect, the present invention provides a dynamic process which maximizes recovery of an alkanolamine from a wash or scrubbing stream used to remove acid gases from gas streams.

In yet another aspect, the present invention provides a combined reaction/reclaiming process for the recovery of an alkanolamine from a scrubbing or washing solution used to remove acid gases from gas streams.

These and further features and advantages of the present invention will become apparent from the following detailed description, wherein reference is made to the figures in the accompanying drawings.

DETAILED DESCRIPTION OF PREFERRED EMBODIMENTS

While the invention will be described with respect to the recovery of DGA from a wash solution used to scrub acid gases from gas streams, particularly hydrocarbon streams, it will be understood that it is not so limited.

The process of the present invention can be used to recover any alkanolamine used in a gas scrubbing operation to remove acid gases from gas streams wherein in the reclaiming process to recover the alkanolamine for further use, the alkanolamine can react with carbamate precursors formed during the gas scrubbing operation to irreversibly produce compounds e.g., amine ethers which consume the alkanolamine. Non-limiting examples of alkanolamines include monoethanolamine (MEA), diethanolamine (DEA), diglycolamine (DGA), methydiethanolamine (MDEA) as well as mixed amines, e.g., mixtures of MDEA and DEA or MEA. It is well known for example that MDEA based mixtures are used to increase the $CO_2$ pickup in cases where the MDEA is allowing too much $CO_2$ to slip overhead in the absorber. Accordingly, spiking the MDEA with MEA or DEA provides advantages.

Figure 1:
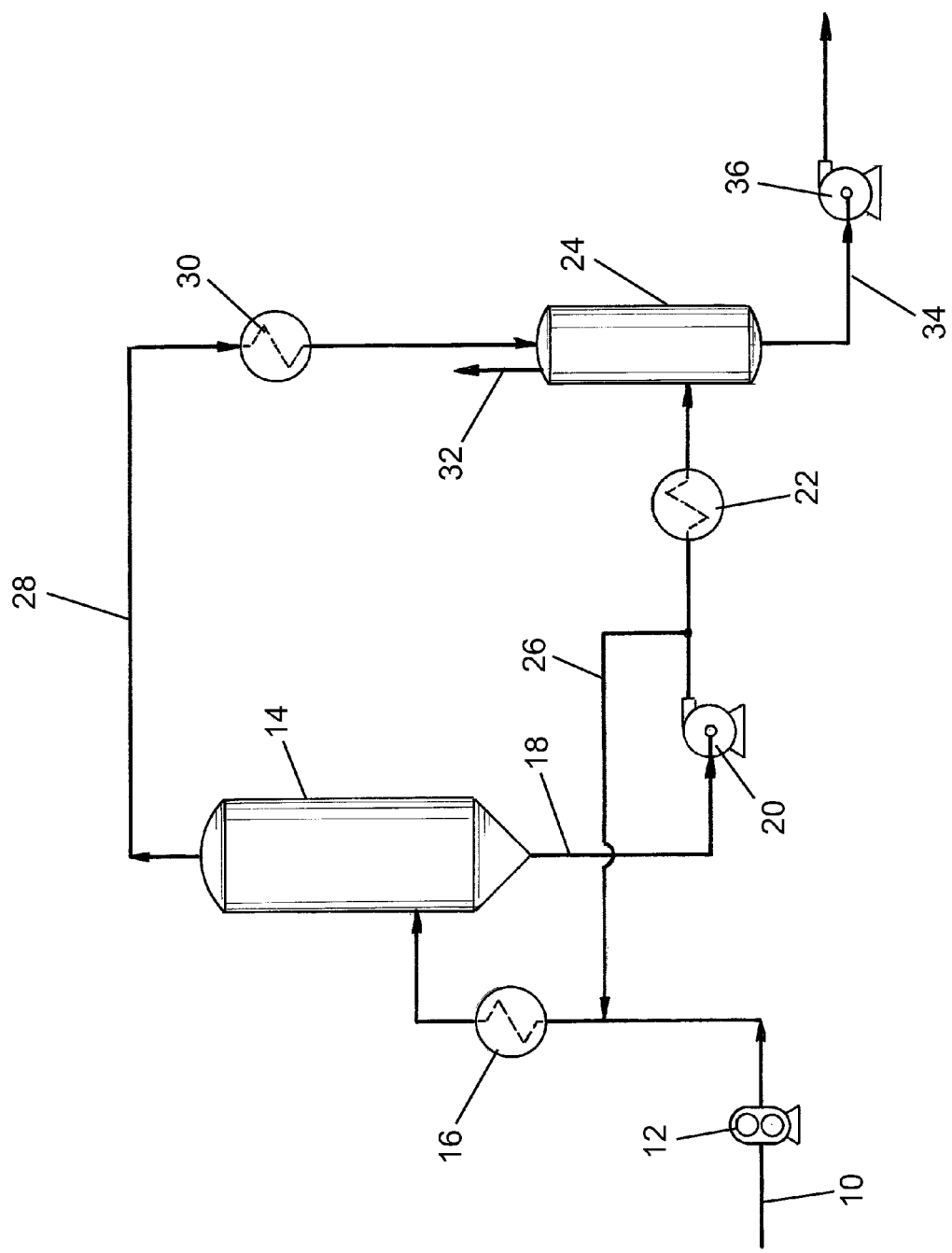
FIG. 1 shows a schematic flow sheet of one embodiment of the process of the present invention.

Referring now to the figures and particularly FIG. 1, a spent gas scrubbing medium comprising DGA, water, carbamate precursors and other contaminants and byproducts removed from the scrubbing operation is introduced via line 10 and pump 12 into reaction vessel 14, the feed stream in line 10 passing through an exchanger 16 where it is preheated prior to entering the reaction zone in vessel 14. Exchanger 16 can be heated in any suitable fashion well known to those skilled in the art.

The reaction zone in vessel 14 is conducted at a positive pressure which can range up to 250 psig and at a temperature of from about 250° F. to about 400° F. depending upon the composition of the feed stream. A product stream is removed from the reaction zone in vessel 14 via line 18 and is pumped by pump 20 through an exchanger 22 into a product tank 24. A portion of the product stream in line 18 is recycled via line 26 to the incoming feed stream in line 10 prior to heat exchanger 16.

An overhead stream of $CO_2$, water and some DGA is removed from vessel 14 and transferred via line 28 and exchanger 30 into product tank 24. In exchanger 30, carried over DGA is condensed and in this regard the cooling medium can comprise the feed stream being introduced via line 10. This feed stream can also be used as the cooling medium in exchanger 22. $CO_2$ is vented from product tank 24 via line 32 while product in product tank 24 is removed via line 34 and pumped via line 36 into storage for further use or back into the gas scrubbing process.

As noted above from this description, the feed stream is being recirculated in the reaction zone in vessel 14 by virtue of the recycle loop comprised of line 18, pump 20, and line 26. It is this recycle loop which controls the residence time of the feed mixture in the reaction vessel 14 and which ensures that the amount of amine ethers being made is minimized and that there is maximum recovery of the DGA. It will be recognized that the residence time is also controlled by the composition of the feed mixture. In this regard, the incoming feed can be monitored to determine the amount of BHEEU. Alternatively, or concomitantly, the product stream exiting reaction vessel 14 via line 18 can also be monitored to determine its composition so as to increase or decrease temperature and the recycle time as necessary.

Accordingly, temperature, recycle rate and hence residence time in the reaction zone in reaction vessel 14 are optimized to, in the case of the use of DGA, minimize the make of morpholine.

In this regard, the reactor provides sufficient residence time, e.g. from about 0.5 to 1 hour, to allow the reaction of BHEEU to DGA to go to completion. As was noted above, the reaction of BHEEU to form DGA and morpholine is favored at high temperatures. Accordingly, it has been found that one of the better methods to control temperature in the reaction zone is by the use of steam at about 100 to 175 psig to ensure that temperatures of 400° F., preferably 365° F., or higher are avoided. If higher pressure (hotter) steam or alternate heat mediums are used then the temperature must be carefully controlled. All in all, the system is operated such that overheating in the reaction zone is avoided.

Figure 2:
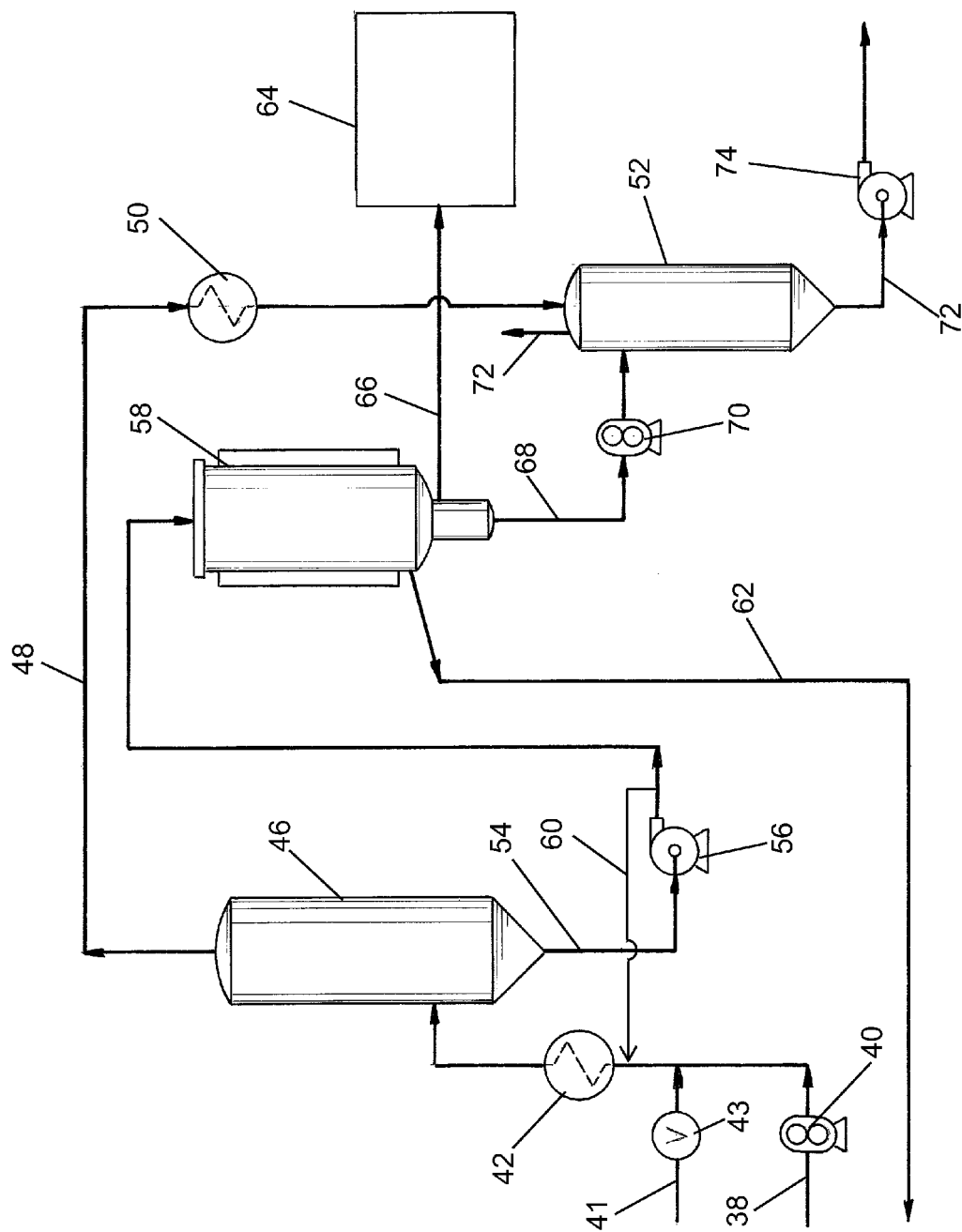
FIG. 2 shows a schematic flow sheet of another embodiment of the process of the present invention.
Figure 3:
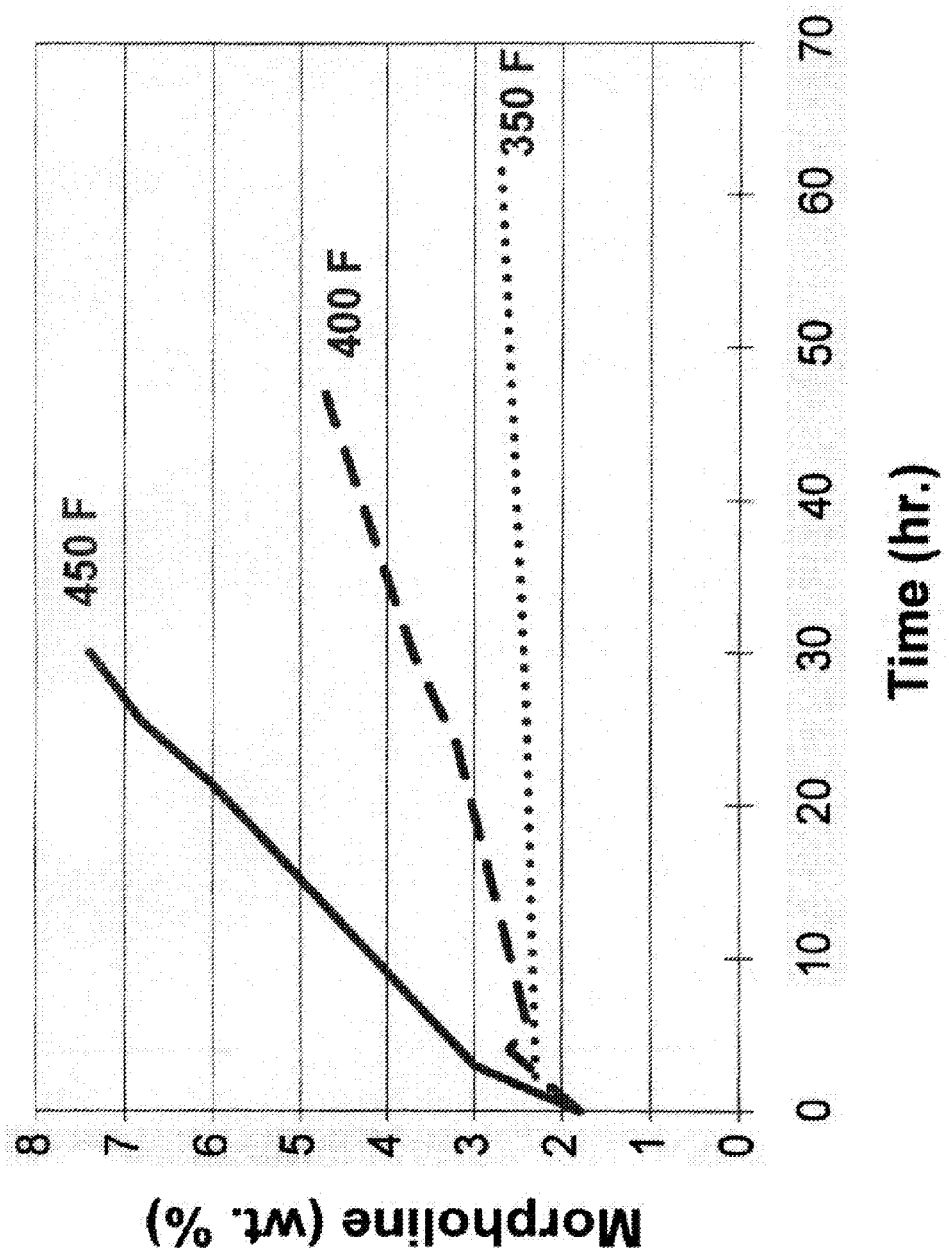
FIG. 3 is a graph taken from a paper entitled "Saudi Arabian Experience with DGA Units and Related Sulfur Platns", Lewis G. Harruff Saudi Arabian Oil Co., (1998) on showing the effect of morpholine formation as a function of temperature.

Referring now to FIG. 2, there is shown another embodiment of the present invention wherein reaction vessel 14 is used as a pressurized flash tank. The feed stream comprising DGA, water, carbamate precursor and other contaminants from the gas scrubbing operation is introduced via line 38, pump 40 and exchanger 42 into flash tank 46. As noted, flash tank 46 is operated under pressure and the residence time of the circulating feed mixture in vessel 46 will generally be as described above with respect to the embodiment shown in FIG. 1, i.e., residence times will again be maintained to be within 0.5 to 1 hour, as discussed above, vessel 46 being operated in a temperature range of from about 330° F. to about 380° F. to ensure best conversion and hydrolysis of the BHEEU. Heat exchanger 42 requires either 250° F., 250 psig steam or some alternate heating medium, such as hot oil, and will operate at about 388° F. (in general greater than 330° F.) to provide the additional heat of vaporization required in flash vessel 46. In operation, the feed stream in flash vessel 46 is flashed and is therefore held at a substantially constant temperature of from about 330° F. to about 375° F., preferably about 360° F.

The overhead flashed stream from flash vessel 46 is removed via line 48 and transferred through cooling condenser 50 into product tank 52. To maximize DGA recovery and handle residue, a bottoms stream is removed from flash vessel 46 via line 54 and transferred via pump 56 into a wiped film evaporator 58. A portion of the stream in line 54 is recycled via recycle line 60 into feed stream 38 and then into flash vessel 46.

It may be necessary to introduce a caustic solution into flash vessel 46. To this end, there is a line 41 having a valve 43 such that the amount of caustic or alkaline solution introduced into flash vessel 46 can be controlled.

It will be appreciated that the bottoms stream leaving flash vessel 46 via line 54, although containing primarily unwanted residue, also contains significant amounts of DGA. Accordingly, the liquid from the flash tank 46 leaving via line 54 is treated in wiped film evaporator 58. Wiped film evaporator 58 is operated under vacuum, e.g., from about 760 to 1 TOR. In wiped film evaporator 58, the residue is further concentrated and removed as a waste stream 62 and sent for suitable disposal. In most cases, about 20% of the feed to flash tank 46 is slip streamed into wiped film evaporator 58 to provide additional concentration of residue. Vacuum conditions in wiped film evaporator 58 are provided by a vacuum system, shown generally as 64, via line 66. It will be appreciated that the vacuum can be provided by steam jets, a vacuum pump, etc. and that vacuum system 64 can include the usual vacuum train to recover materials removed from wiped film evaporator 58.

Since wiped film evaporator 58 has an integral condenser, the DGA is condensed and transferred via line 68 and pump 70 into product tank 52. Again, product tank 52 is provided with a vent 72 for $CO_2$ and any other uncondensable gases. Product from product tank 52 can be transferred via line 72 and pump 74 back into the gas processing operation or for storage and later use. It will be appreciated that the vacuum system 64 may recover waste products which can be transferred to waste stream 62 for appropriate disposal. It will further be appreciated that various valves, gauges, etc., commonly used have not been shown for simplicity's sake.

As can be seen from the above, the present invention provides a dynamic reaction process which avoids loss of DGA by maximizing the conversion of BHEEU and the subsequent recovery of the DGA. Additionally, the present invention provides such a dynamic reaction system in conjunction with a waste recovery system, using a wiped film evaporator, to further recover DGA and remove waste from the system for proper disposal.

Although specific embodiments of the invention have been described herein in some detail, this has been done solely for the purposes of explaining the various aspects of the invention, and is not intended to limit the scope of the invention as defined in the claims which follow. Those skilled in the art will understand that the embodiment shown and described is exemplary, and various other substitutions, alterations and modifications, including but not limited to those design alternatives specifically discussed herein, may be made in the practice of the invention without departing from its scope.

What is claimed is:

1. A process for recovering an alkanolamine from a wash stream used to remove acid gases from a gas stream, comprising:
   introducing a fluid stream comprising water, a linear ether alkanolamine, and up to about 20 wt % carbamate precursor into a reaction zone maintained at a positive pressure and at a temperature of from about 250° F. to about 400° F.;
   circulating said fluid stream through said reaction zone at a rate to provide a residence time of from about 0.5 to about 1 hour of said fluid stream in said reaction zone to convert at least a portion of said carbamate precursor to said alkanolamine and carbon dioxide and reduce the formation of amine ethers;
   recovering a product stream from said reaction zone comprising water, carbon dioxide and alkanolamine;
   recycling a portion of said product stream to said fluid stream to at least partially control the residence time of said fluid stream in said reaction zone.

2. The process of claim 1, wherein said pressure is up to about 250 psig.

3. The process of claim 1, wherein said fluid stream is heated prior to introduction into said reaction zone.

4. The process of claim 1, wherein said fluid stream comprises from about 0 wt % to about 20 wt % of carbamate precursor and from about 40 wt % to about 50 wt % alkanolamine.

5. The process of claim 1, wherein said product stream comprises less than about 4 wt % carbamate precursor.

6. The process of claim 1, wherein the amount of carbamate precursor present in said fluid stream is monitored.

7. The process of claim 1, wherein said alkanolamine is diglycol amine.

8. The process of claim 1, wherein said process is continuous.

9. The process of claim 1, wherein said gas stream is a hydrocarbon gas stream.

10. A process for recovering an alkanolamine from a wash stream used to remove acid gases from a gas stream, comprising:
    introducing a fluid stream comprising water, a linear ether alkanolamine, and up to about 20 wt % carbamate precursor into a pressurized reaction zone, said reaction zone being at a temperature of from about 250° F. to about 400° F.;
    circulating said fluid stream through said reaction zone at a rate to provide a residence time of from about 0.5 to about 1 hour of said fluid stream in said pressurized reaction zone to convert at least a portion of said carbamate precursor to said alkanolamine and carbon dioxide and reduce formation of amine ethers;
    recovering a first product stream from said pressurized reaction zone, said first product stream comprising water, carbon dioxide, and alkanolamine;
    recycling a portion of said first product stream to said fluid stream to at least partially control residence time of said fluid stream in said reaction zone;
    removing a bottoms stream from said pressurized reaction zone;
    introducing said bottoms stream into a wiped film evaporator operated under vacuum;
    recovering a second product stream from said wiped film evaporator.

11. The process of claim 10, wherein said pressure is up to about 250 psig.

12. The process of claim 10, wherein said fluid stream is heated prior to introduction into said reaction zone.

13. The process of claim 10, wherein said fluid stream comprises from about 40 wt % to about 50 wt % alkanolamine.

14. The process of claim 10, wherein said product stream comprises less than about 4 wt % carbamate precursor.

15. The process of claim 10, wherein the amount of carbamate precursor present in said fluid stream is monitored.

16. The process of claim 10, wherein said alkanolamine is diglycol amine.

17. The process of claim 10, wherein said process is continuous.

18. The process of claim 10, wherein said gas stream is a hydrocarbon gas stream.

* * * * *